United States Patent [19]

Lester

[11] 4,054,622

[45] Oct. 18, 1977

[54] COMBINATION NEBULIZER AND HUMIDIFIER

[76] Inventor: Victor E. Lester, P.O. Box 608, Sanora, Calif. 95370

[21] Appl. No.: 86,433

[22] Filed: Nov. 3, 1970

[51] Int. Cl.$^2$ .......................................... A61M 11/00
[52] U.S. Cl. ................................. 261/64 R; 128/194; 251/310; 261/78 A; 261/124; 261/DIG. 65
[58] Field of Search .................... 128/194, 186, 188; 261/64 R, 78 A, 124, DIG. 65; 251/310, 311

[56] References Cited

U.S. PATENT DOCUMENTS

| | | | |
|---|---|---|---|
| 1,272,943 | 7/1918 | Gordon | 251/310 |
| 2,580,575 | 1/1952 | Muckler | 251/310 |
| 2,678,044 | 5/1954 | Szekely et al. | 128/194 |
| 2,869,188 | 1/1959 | Cameto | 128/186 |
| 3,066,923 | 12/1962 | Boteler | 261/64 R |
| 3,206,175 | 9/1965 | Boteler | 128/194 |
| 3,353,536 | 11/1967 | Bird et al. | 128/194 |
| 3,522,806 | 8/1970 | Szekley | 128/194 |
| 3,572,660 | 3/1971 | Mahon | 128/194 |

FOREIGN PATENT DOCUMENTS

| | | | |
|---|---|---|---|
| 88,403 | 1/1960 | Denmark | 128/194 |
| 1,143,548 | 2/1969 | United Kingdom | 128/188 |

*Primary Examiner*—Tim R. Miles
*Attorney, Agent, or Firm*—Lyon & Lyon

[57] ABSTRACT

A self-contained disposable unit for converting a liquid to aerosol or for humidifying a gas includes gas inlet means and an enclosed container having a liquid supply reservoir and an outlet for the aerosol or for the humidified gas. A nozzle assembly for producing aerosol extends into the container above the liquid supply reservoir and a dual purpose conduit in communication with the liquid supply reservoir either carries liquid from the reservoir to the nozzle assembly during nebulization or passes gas into the liquid in the reservoir during humidification. The unit also includes valve means for selectively diverting gas from the gas inlet means to the nozzle assembly for nebulization or through the dual purpose conduit into the liquid in the liquid supply reservoir for humidification.

29 Claims, 8 Drawing Figures

U.S. Patent  Oct. 18, 1977  Sheet 1 of 2  4,054,622
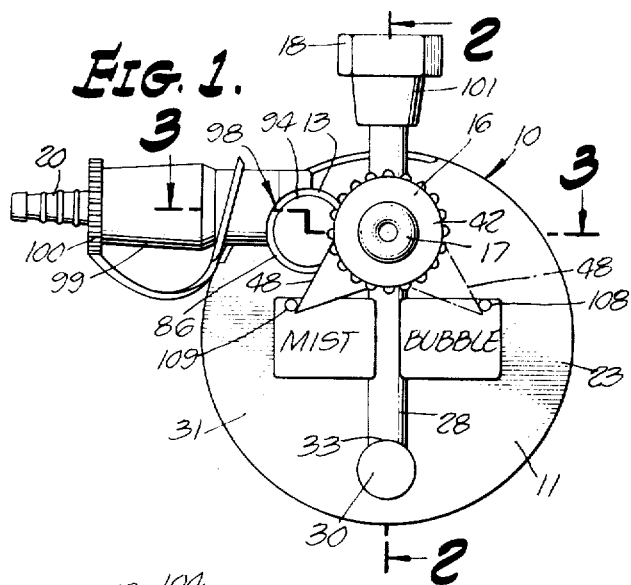
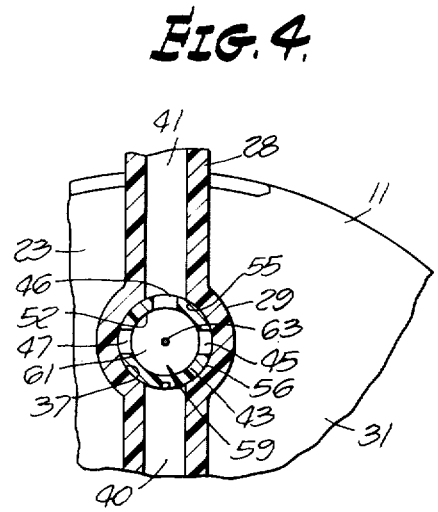
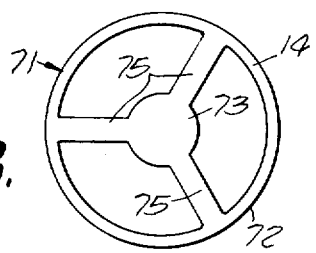
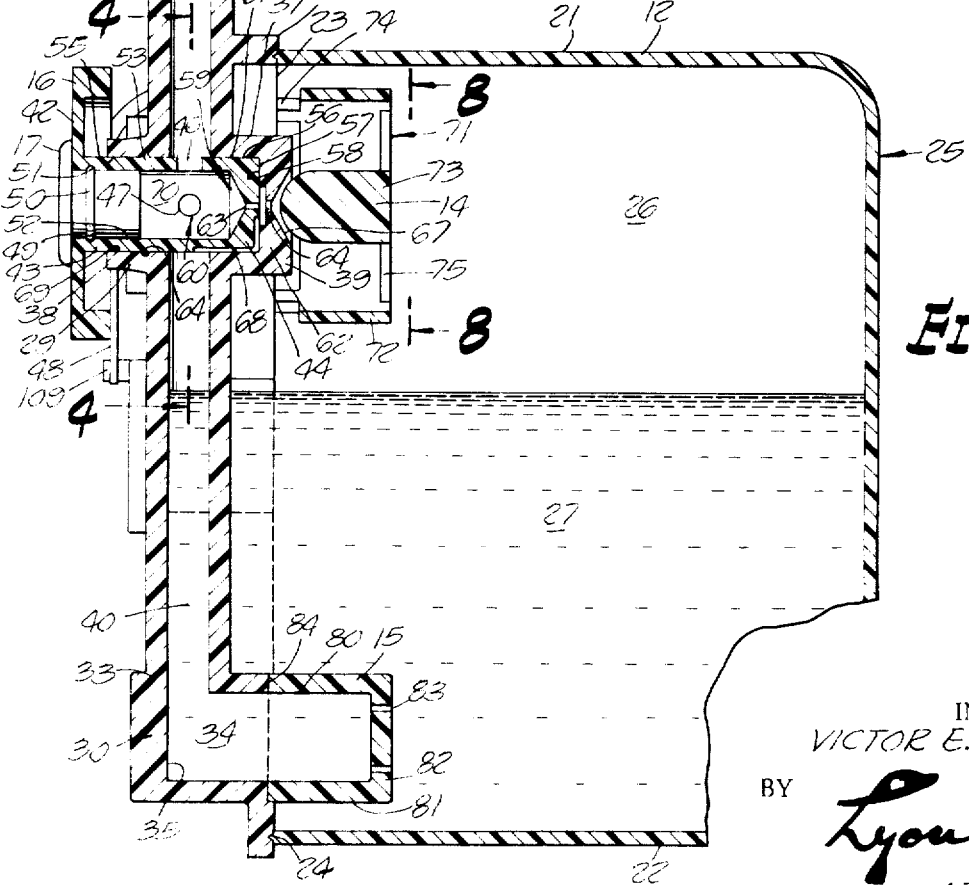
INVENTOR
VICTOR E. LESTER
BY Lyon+Lyon
ATTORNEYS

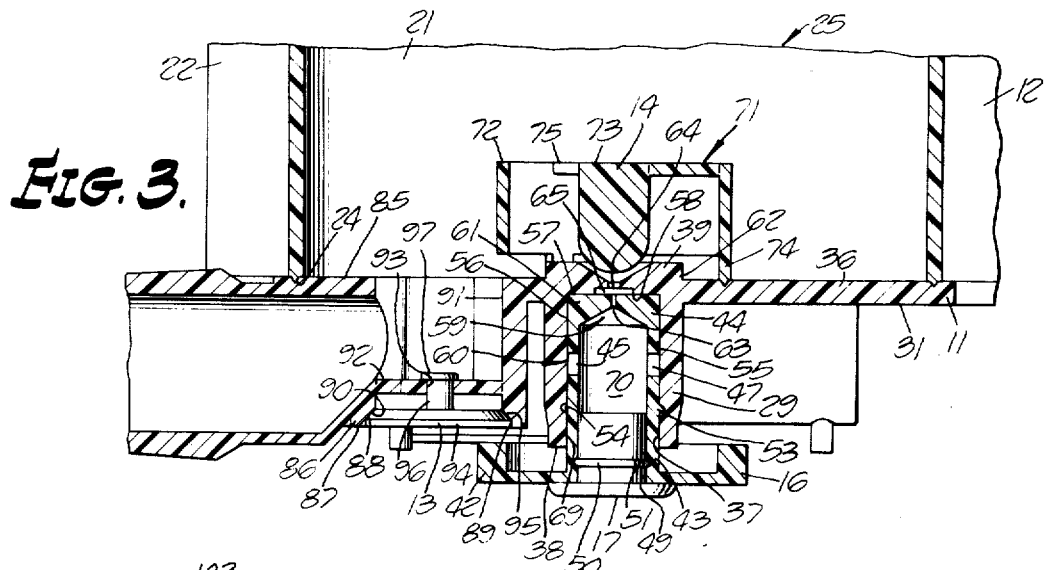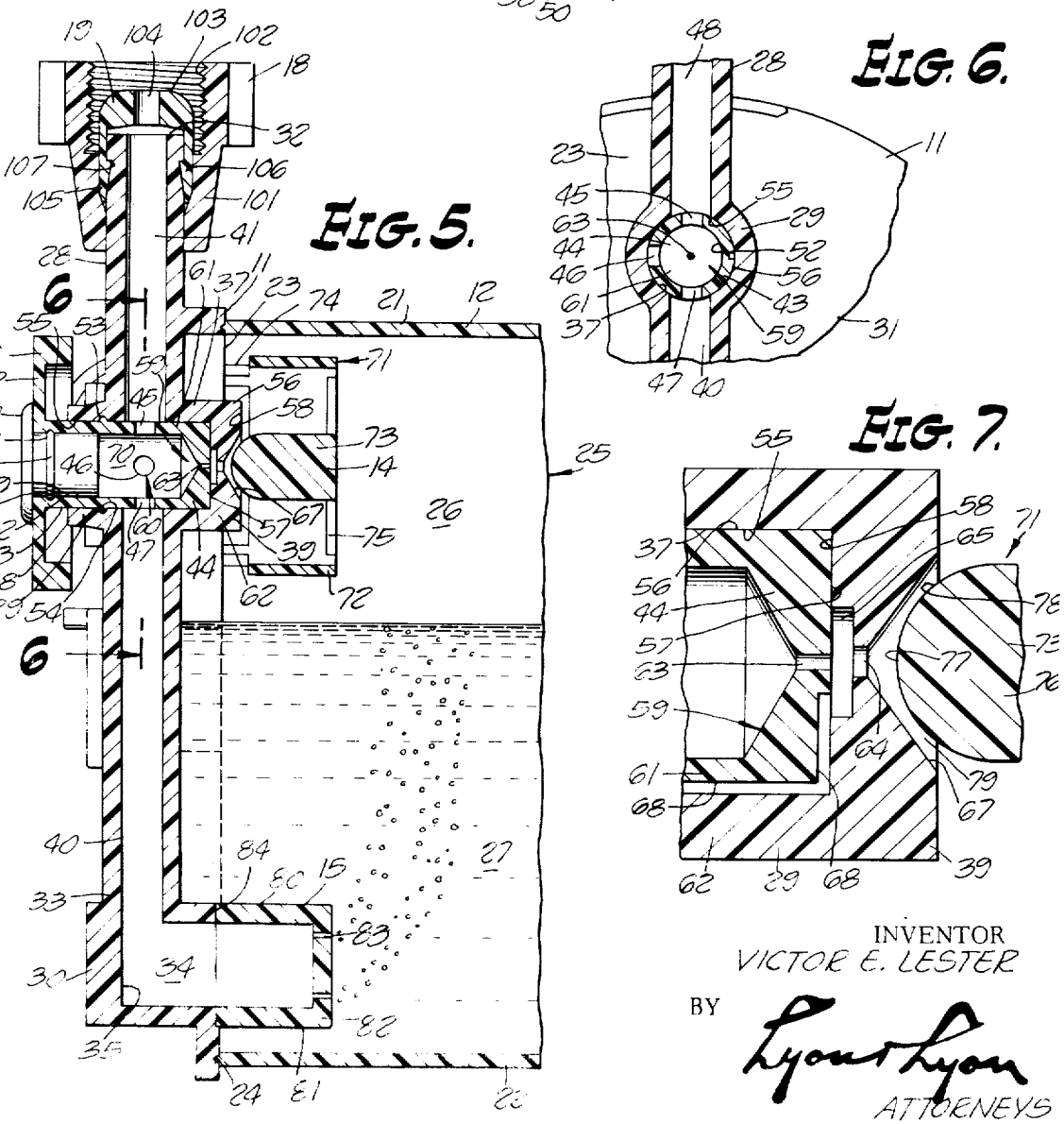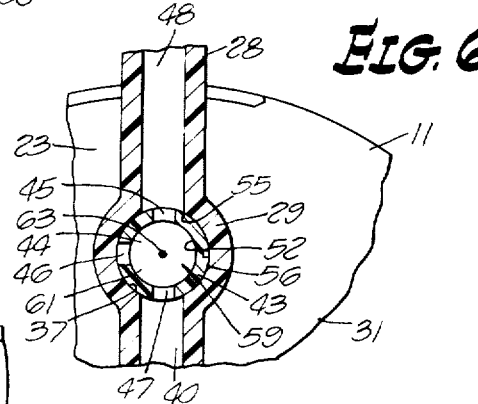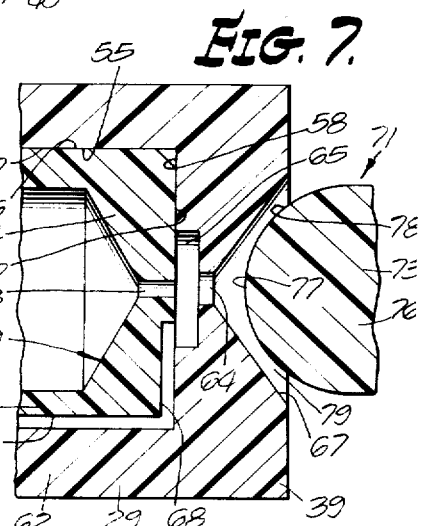

COMBINATION NEBULIZER AND HUMIDIFIER

This invention relates to a vapor producing device and more particularly relates to a self-contained combination nebulizer and humidifier unit for use in inhalation therapy.

Inhalation therapy often requires the use of either a nebulizer or a humidifier or both depending on the nature of the illness being treated. Humidifiers increase the relative humidity of dry gases by about 10 to 50 percent by bubbling the gases through a liquid and such humidifiers are very useful when the inhalation treatment involves the administration of oxygen or mixtures of oxygen and other gases to a patient. Pure oxygen when obtained from a usual supply tank source is extremely dry, having a relative moisture or humidity content of less than about 2 percent. Preferably, breathable oxygen and oxygen mixtures should have a relative humidity of at least 30 percent and a higher relative humidity is often therapeutically desirable since it has been found that the increased relative humidity reduces the content of bacteria and dust and thereby minimizes pathogens. Moreover, if the gas entering the patient is too dry it may cause serious drying of the naturally moist membranes within the nose, sinuses, mouth, throat, and respiratory tracts which can compound respiratory ailments.

When the inhalation therapy requires the administration of an aerosol mist a nebulizer is necessary. Nebulizers are pneumatic devices for breaking up a liquid medicament into small particles and entraining the small liquid particles in a gas stream. It is important during nebulization that there be a sufficient quantity and proper formation of aerosol provided by the nebulizer. If the particles or droplets of the medicament are too fine, they are not likely to be retained in the respiratory tract, but will, to a great extent, be exhaled. If the particles are too large, they will likely be deposited on the upper reaches of the respiratory system, such as the trachea and the upper tracheal-bronchial tree, thereby leaving the rest of the system untreated. It is also important that the aerosol be delivered to the patient in a smooth, uniform manner.

A number of devices for producing aerosol and a number of devices for humidifying gases have been proposed, however, because of the different operations involved, nebulizers and humidifiers in the past have typically been separate units. It has also been common to employ the fly-spray principle of aerosol in the design of the nebulizers. This principle involves directing a stream of gas from a nozzle at right angles across the open end of a tube running to the liquid medicament. Proper positioning and sizing of the tube and nozzle are extremely critical and the design of a nebulizer employing this principle is such that it is difficult and expensive to manufacture, particularly if the nebulizer is to be made of plastic.

Therefore, fly-spray nebulizers are often made of glass and are very delicate and must be handled with a great degree of care. However, because of the relatively high cost of such nebulizers it is not practical to dispose of them after use and therefore these nebulizers must undergo costly periodic cleaning.

On the other hand, a nebulizer involving the principles of my U.S. Pat. No. 3,097,645 and my United States Patent Application Ser. No. 86,525 filed on Nov. 3, 1970, now U.S. Pat. No. 3,762,409, is easily formed of plastic and therefore is relatively inexpensive to produce.

Therefore, it is a primary object of the present invention to provide an inexpensive to manufacture and therefore disposable device which will selectively perform both the operations of a nebulizer and humidifier. In accordance with this object it is desirable to incorporate within the present invention many of those principles relating to a nebulizer which are included in my previously mentioned U.S. Pat. No. 3,097,645 and my United States Patent Application Ser. No. 86,525. This and other objects and advantages will be apparent from the accompanying drawings and following detailed description.

Briefly, however, the present invention includes gas inlet means and an enclosed container having a liquid supply reservoir and an outlet for the aerosol or humidified gas. A nozzle assembly for producing the aerosol having a gas nozzle and a spray nozzle with spaced and coaxially positioned orifices extends into the container above the liquid supply reservoir and a dual purpose conduit extending from the nozzle assembly is in communication with the liquid supply reservoir. Selective operation of the unit as either a nebulizer or as a humidifier is dependent on valve means which, when aerosol is desired, causes gas from the gas inlet means to enter the gas nozzle whereby liquid from the liquid supply reservoir is communicated through the dual purpose conduit into the spray nozzle or, when humidified gas is desired, diverts gas from the gas inlet means directly into the dual purpose conduit which communicates the gas to the liquid supply reservoir. A diffuser-baffle assembly cooperates with the nozzle assembly to promote and improve the production of aerosol.

In the drawings:

FIG. 1 is a elevation view of the device.

FIG. 2 is a side sectional view of the device taken substantially on the lines 2—2 of FIG. 1 illustrating the valve means during nebulization and the dual purpose conduit.

FIG. 3 is a fragmentary view in section taken substantially on the lines 3—3 of FIG. 1 illustrating the diffuser baffle assembly.

FIG. 4 is a fragmentary view in section taken substantially on the lines 4—4 of FIG. 2 illustrating the position of the valve means during nebulization.

FIG. 5 is a side sectional view of the device similar to FIG. 2 illustrating the valve means during humidification and the dual purpose conduit.

FIG. 6 is a fragmentary view in section taken substantially on the lines 6—6 of FIG. 5 illustrating the position of the valve means during humidification.

FIG. 7 is an enlarged fragmentary view in section illustrating the nozzle assembly and the cooperating diffuser-baffle assembly.

FIG. 8 is a plan view taken substantially on the lines 8—8 of FIG. 7 illustrating the diffuser-baffle assembly.

Referring now in detail to the drawings, the combination nebulizer and humidifier unit or device, generally designated 10, is preferably constructed of a plastic material and comprises essentially seven separately molded components; a cover component 11, a container component 12, a safety valve component 13, a diffuser-baffle component 14, a gas disseminator component 15, a valve and gas nozzle component 16, and a valve cap component 17. Three other separately molded components also shown in the drawings but which are less important with regard to the operation of the unit 10 are a gas inlet connector component 18, a gas inlet seal component 19, and an outlet connector component 20. It should be noted that the cover component 11, container component 12, diffuser-baffle component 14, gas disseminator component 15, and the gas inlet connector component 18 are of a relatively hard plastic material, such as crystal polystyrene, whereas the safety valve component 13, valve and spray nozzle component 16, the valve cap component 17, the gas inlet seal component 19, and the outlet connector component 20 are of a somewhat flexible plastic material, such as polyethylene. Because of their particular design and shape, each component can be quickly and easily injection-molded and then assembled without the need for extensive additional machining. During assembly the relatively hard plastic components are connected together by any suitable means, as for example by an ultra-sonic sealing process or by an adhesive. However, because of the nature of the material and the design of the components, the flexible plastic components can be press fitted onto the other components for a connection therebetween.

The container component 12 is preferably transparent and comprises a cylindrical bowl 21 having a cylindrical sidewall 22. The cover component 11 includes a flat circular disc 23 which is secured to the edge 24 of the sidewall 22 to cover the bowl 21. Thus the bowl 21 and the disc 23 define an enclosed container, generally designated 25, having an upper receiving area 26 and a lower liquid supply reservoir area 27. It should be noted that during the operation of the unit 10 the bowl is in a sideways position with the disc 23 forming a side enclosure.

The cover component 11 also includes an integrally formed tube 28, cylindrical sleeve 29 and an enclosed hollow cylindrical boss 30. The tube 28 is centrally positioned on the disc 23 and extends parallel to the outer surface 31 of the flat disc 23 from an upper end 32 beyond the top of the enclosed container 25 to a lower end 33 adjacent the liquid supply reservoir 27. The cylindrical sleeve 29 and cylindrical boss 30 both project outwardly from the outer surface 31 of the disc 23 and the lower end 33 of the tube 28 is received by the boss 30 and a section of the tube 28 adjacent the receiving area 27 of the enclosed container 25 is interrupted by the sleeve 29. The boss 30 defines an inlet chamber 34 which is closed at the outwardly extending end 35 of the boss and open at the lower end 33 of the tube and at the inner surface 36 of the disc 23. The sleeve 29 defines a receptacle 37 which is open at the outwardly extending end 38 of the sleeve and terminates at an end wall 39 which protrudes beyond the inner surface of the disc 23 into the receiving area 27. The tube 30 and inlet chamber 34 define a lower passageway or dual purpose conduit 40, the purpose of which is hereafter described, which extends from the liquid supply reservoir area 27 to the receptacle 37 and the tube 30 also defines an upper passageway or gas inlet conduit 41 which extends from the receptacle 37 to the upper end 32 of the tube and which is in parallel alignment with the lower passageway 40.

The valve and gas nozzle component 16 includes a turning knob 42, a centrally positioned tubular extension 43 having an end wall 44 and three side ports 45, 46 and 47, and an indicator 48. The open end 49 of the tubular extension 43 is enclosed and sealed by the valve cap component 17 which includes an annular flange 50 which is press fitted into an annular groove 51 on the inner surface 52 of the tubular extension 43. The tubular extension 43 is adapted to fit into the receptacle 37 with the ports 45, 46 and 47 being positioned at the level of the passageways 40 and 41 and the knob 42 extending over the end of the sleeve 29. The tubular extension 43 includes an annular flange 53 which is press fitted into an annular groove 54 on the inner surface 55 of the sleeve 29 thereby preventing axial movement while permitting rotational movement of the tubular extension 43 in the receptacle 37 and the indicator 48 indicates the relative position of the ports 45, 46 and 47 with respect to the passageways 40 and 41. The outer surface 56 of the tubular extension 43 and the outer surface 57 of the end wall 44 fit tightly against the inner surface 55 of the sleeve 29 and the inner surface 58 of the end wall 39, respectively, to prevent leakage therebetween.

Thus, the tubular extension 43 of the valve and gas nozzle component 16 and the receptacle 37 of the cover component 11 cooperate to form both the nebulizer nozzle assembly, generally designated 59, and the valve assembly generally designated 60.

The nozzle assembly 59 includes an inner gas nozzle 61 formed by the forward portion of the tubular extension 43 and the end wall 44 and an outer spray nozzle 62 formed by the forward portion of the receptacle 37 and the end wall 39. The end wall 44 includes a centrally positioned gas orifice 63 and the end wall 39 includes a centrally positioned spray orifice 64 which is coaxial with the gas orifice 63. The end wall 39 is also provided with a cylindrical recess 65 on its inner surface 58 which thereby defines a space between the two orifices 63 and 64 and its outer surface 66 is provided with a frusto-conical recess 67 which is coaxial with and surrounds the spray orifice 64. The outer surface 57 of the end wall 44 and the outer surface 56 of the tubular extension 43 are provided with a groove 68 which extends from the level of the passageway 40 to the space formed by the cylindrical recess 65.

The diameters of the gas orifice 63 and spray orifice 64 is an important aspect in obtaining proper nebulization. In determining the diameter of each orifice, consideration must be given to the rate of gas flow and viscosity of the liquid medicament to be nebulized. When the gas flow is between about 3 to 8 liters per minute and the viscosity of the liquid is approximately that of water, a gas orifice diameter within the range of about 0.024 and 0.028 and a spray orifice diameter within the range of about 0.036 and 0.042 is preferable. If the gas flow rate is extended outside these limits, and/or a more viscous liquid is used, then compensation of the diameters should be made to obtain the desired aerosolization.

Along with the foregoing relationship of the spray orifice diameter and gas orifice diameter, the space between the orifices 63 and 64 as provided by the cylindrical recess 65 should be between about 0.012 and 0.015 inch. It has been found that if this space or distance is greater than 0.015 inch large droplets are produced instead of a fine aerosol. Also of importance is the distance between the inner surface 58 and the outer surface 66 of the end wall 39 at the edge of the spray orifice 64. In accordance with the gas flow and the liquid viscosity set forth above it is preferable that this distance be about 0.015 inch in order to prevent noise when spray eminates from the spray orifice 64. By providing the frusto-conical recess 67 this distance at the edge of the spray orifice 64 is achieved without interfering with forming of the end wall 39 by the injection-molding process.

The valve assembly 60 includes a valve housing 69 formed by the receptacle 37 and a valve chamber 70 formed by the interior of the tubular extension 43. Side port 45 circumferentially spaced 180° from side port 47 and in alignment therewith provides for communication between the passageway 41 and the valve chamber 70 when the side port 47 is in alignment with the passageway 40. Side port 46 circumferentially spaced 90° from side port 45 and 180° from the groove 68 on the outer surface 56 of the tubular extension 43 provides communication between the passageway 41 and the valve chamber 70 when the groove 68 is aligned with the passageway 40.

The diffuser-baffle component 14 is secured to the cover component 11 and defines a diffuser-baffle assembly, generally designated 71. The diffuser-baffle assembly 71 includes a cylindrical baffle plate 72 having three equally spaced legs 74 which are connected to the inner surface 36 of the disc 23 around the end wall 39 and thereby coaxially position the baffle plate 72 with respect to spray orifice 64. The diffuser-baffle assembly 71 also includes a diffuser member 73 which is supported at one end by a three equally spaced spokes 75 which extend radially inward from the baffle plate 72. The other end of the diffuser member 73 comprises a nose portion 76 spaced from the spray orifice 64 with its furthermost extension 77 extending into the frusto-conical recess 67 about 0.030 inch from the spray orifice 64 and being coaxial therewith. The nose portion 76 includes a generally rounded surface of revolution 78 diverging from the furthermost extension 77 away from the spray orifice 64 thereby defining a path 79 for the aerosol spray emanating from the spray orifice 64 between the surface of the recess 67 and the surface of the nose portion 76.

The gas disseminator component 15 is also secured to the cover component 11 and defines a disseminator cap 80 which covers the open end of the inlet chamber 34 at the inner surface of the disc 23. The cap 80 extends into the liquid supply reservoir area 27 and includes a cylindrical sidewall 81 and an end wall 82 having a plurality of relatively small apertures 83. The inner surface 36 of the disc 23 is provided with an annular recess 84 surrounding the opening of the inlet 34 which receives the edge of the sidewall 81 for a connection therebetween.

The cover component 11 also includes an outlet opening 85 extending through the disc 23. Extending outwardly from the outer surface 31 of the disc is an integrally molded generally cylindrical hollow boss 86 coaxial with the opening 85 and open at its outwardly extending end 87. The end 87 is provided with an annular recess 88 having a cylindrical section 89 which extends inwardly from the end 87 to a frusto-conical section 90 which extends inwardly to the inner surface 91 of the boss 86. A support 92 having a central opening 93 extends across the inner surface 91 adjacent the open end 87 and inward from the recess 88. The safety valve component 13 comprises a flat relatively thin disc 94 with its edge or side 95 being shaped to conform to the annular recess 88 and includes a centrally positioned cylindrical extension 96 with an annular flange 97 at its end. The disc 94 is adapted to cover the open end 87 of the boss 86 with the side 95 fitting into the annular recess 88 and the extension 96 extending through the central opening 93 of the support 92 and held in position by the flange 97. The boss 86 and the safety valve component 13 when assembled in this fashion form a safety valve assembly, generally designated 98, the purpose of which will be described hereafter.

In communication with the interior of the boss 86 and therefore in communication with the outlet opening 85 is an outlet tube 99 which is an integrally formed part of the cover component 11. The outlet tube 99 extends from the boss 86 parallel to the plane of the disc 23 and substantially perpendicular to the tube 28 to an open end 100 beyond the enclosed container 25. The open end 100 is adapted to receive the outlet connector component 20 or any other suitable means for connecting the outlet tube 99 to a mask or other unit extending to the patient's face.

The gas inlet connector component 18 and seal component 19 are connected to the upper end 32 of the tube 28. The connector component 18 includes a tapered sleeve 101 which fits slidably around the tube 28 and an internally threaded bore 102 which extends beyond the upper end 32 of the tube. The seal component 19 comprises an end wall 103 having a central opening 104 and a side wall 105. The end wall 103 fits up against the end 32 of the tube with the opening 104 in matched alignment with the passageway 41 and the side wall 105 fits coaxially about the tube 28 between the tube 128 and the tapered sleeve 101 of the connector component 18. The inner surface of the side wall 105 is provided with an annular ridge 106 which is press fitted into an annular recess 107 on the tube. When the threaded end of the connector component 18 is secured to an externally threaded conduit (not shown) for communication of compressed gas from a suitable source to the gas inlet conduit 41, the end wall 103 of the seal component 19 is pressed against the end of the tube and the tapered sleeve 101 forces the side wall 103 of the seal component 19 against the tube 28 to create an air-tight seal therebetween.

The cover component 11 is also provided with a pair of outwardly protruding stops 108 and 109 against which the indicator 48 contacts when the valve ports 45 and 47 are rotated into alignment with the passageways 41 and 40 or when the valve port 46 and the groove 68 are rotated into alignment with the passageways 41 and 40.

In operation, the reservoir 27 of the enclosed container is filled to a level below the spray orifice 64 with a desired liquid. The inlet connector component 18 is then secured to the conduit from the compressed gas source and the outlet tube 99 is connected to a mask or other suitable means extending to the patient's face. If nebulization is desired, the knob 42 is turned until the indicator 48 moves into contact with the stop 109 whereupon the valve port 46 is in alignment with the gas inlet conduit 41 and the groove 68 is in alignment with the dual purpose conduit 40. When the valve assembly 60 is in this position, gas from the inlet conduit flows through the valve port 46 into the valve chamber 70. Since the valve ports 45 and 47 are blocked by the inner surface of the sleeve 29 all the gas entering the valve chamber 70 is directed by the valve assembly 60 through the gas nozzle 61 and through the gas orifice 63. As the gas exits out the gas orifice 63, it creates a partial vacuum in the space between the gas orifice 63 and the spray orifice 64. This vacuum causes liquid medicament from the liquid supply reservoir 27 to rise in the dual purpose conduit 40 and flow through the passageway or channel formed between the groove 68 and the inner surface of the spray nozzle 62 into the space 65 between the orifices 63 and 64. When the stream of gas exiting the gas orifice 63 strikes this liquid it entrains it in droplet form and carries it along outwardly through the path 79 which promotes aerosolization. The spray then continues into the receiving area 26 where it strikes the inner surface of the baffle plate 72 to remove oversize droplets of liquid. After the oversize droplets are removed, the aerosol spray eventually migrates around the edge of the baffle plate 72 through the outlet opening 85 and through the outlet tube 99 and then on into the patient's respiratory tract.

If humidification is desired, the knob 42 is turned until the indicator 48 moves into contact with the stop 108 whereupon the valve port 45 is in alignment with the gas inlet conduit 41 and the valve port 47 is in alignment with the dual purpose conduit 40. When the valve assembly 60 is in this position gas from the gas inlet conduit 41 flows through the valve port 45 into the valve chamber 70 and is directed out through the aligned valve port 47 into the conduit 40. A small amount of gas may pass through the gas orifice 63, but it will be rather insignificant because of the relative difference between the size of the orifice 63 and the size of the valve port 47. The gas flow then continues through the conduit 40 into the disseminator cap 80 against the end wall 82. The gas then passes through the small apertures 83 into the liquid supply reservoir area 27 in the form of small bubbles where it picks up moisture as it rises to the surface of the liquid in the liquid supply reservoir 27. The humidified gas then exits from the receiving area 26 of the enclosed container 25 through the outlet opening 85 and then through the outlet tube 99 on into the patient's respiratory tract. From this above description of the operation of the unit 10, it is obvious why the conduit 40 has been designated as a dual purpose conduit; it communicates with the liquid in the supply reservoir 27 and during nebulization it carries the liquid to the nozzle assembly 59 and during humidification it transmits the gas to the disseminator 80. It should also be noted that the apertures 83 are preferably smaller than the passageways or orifices to thereby prevent unwanted particles in the liquid supply reservoir 27 from entering and clogging up the passageways and orifices.

The safety valve assembly 98 also serves a dual purpose. It prevents undue pressure build-up within the enclosed container 25 should the conduit extending between the outlet tube 99 and the patient become constricted or plugged and warns an attendant of such a constriction. Whenever pressure within the enclosed container 25 becomes too great the disc 94 will unseat to provide an outlet opening between the edge or side 95 of the disc 94 and the recess 88 and the gas exiting out through this opening will create a sufficiently loud noise to warn an attendant of the impairment. It should also be noted that a portion 110 of the inner surface of the hollow boss 86 is relieved and sloped downwardly and inwardly in order that any liquid which is directed out through the outlet opening 85 or any condensate that forms on the inner surface of the boss 86 will return to the enclosed container 25.

This invention provides a self-contained combination unit 10 which selectively operates as either a nebulizer or a humidifier without requiring any added elements or any modification of the elements of the unit. Moreover, the novel and unique design of the unit is such that the individual components comprising the unit can each be made of plastic easily and inexpensively by an injection-molding process whereby the cost of production of the unit is relatively cheap and therefore may be disposed of after use. The unit also includes safety features which avoid an unwanted build-up of pressure within the unit and warn an attendant of this impairment.

Having fully described my invention, it is to be understood that I do not wish to be limited to the details herein set forth, but my invention is of the full scope of the appended claims.

I claim:

1. In a humidifier-nebulizer device including an enclosed liquid holding chmaber, means for connecting said device to a gas supply source, conduit means for directing a gas therethrough and a gas exit conduit elevated above the normal liquid level in said liquid holding chamber, the improvement comprising:
    a. an upper conduit for directing gas from a supply source and a lower conduit each of which communicates with a cavity formed in a valve housing, said lower conduit also communicating with the liquid holding chamber adjacent the bottom thereof;
    b. a valve spool received in the valve housing cavity, the spool and the housing cooperating to define a valve chamber therebetween, said spool being selectively aligned between a gas humidification and a nebulization position respectively and having a first passageway system within said valve spool and comprising first and second passageways, the first passageway communicating with said upper conduit and the second passageway communicating with said lower conduit, said first passageway system directing gas from the upper conduit to the lower conduit and into a liquid in said liquid holding chamber when said valve spool is aligned for gas humidification, and a second passageway system comprising third and fourth passageways, the third passageway communicating with said upper conduit and the fourth passageway communicating with said lower conduit, whereby the second passageway system simultaneously directs gas from the upper conduit to the valve chamber through said third passageway and draws liquid from the lower conduit to said valve chamber through said fourth passageway for atomization of said liquid with said gas in said valve chamber when said valve spool is aligned for nebulization; and
    c. an orifice communicating said valve chamber with said liquid holding chamber above the liquid level.

2. In a humidifier-nebulizer device including a liquid holding chamber, means for connecting said device to a gas supply source, and gas exit means elevated above the normal liquid level in said liquid holding chamber, the improvement comprising:
    an upper conduit for directing gas from the supply source and a lower conduit each of which communicates with a cavity formed in a valve housing, said lower conduit also communicating with the liquid holding chamber adjacent the bottom thereof;
    a valve spool received in the valve housing cavity the spool and the housing cooperating to define a valve chamber therebetween, said spool being selectively aligned between a gas humidification and a nebulization position respectively and having a first passageway system within said valve spool and comprising first and second passageways, the first passageway communicating with said upper conduit and the second passageway communicating with said lower conduit said first passageway system directing gas from the upper conduit to the lower conduit and into a liquid in said liquid holding chamber when said valve spool is aligned for gas humidification, and a second passageway system comprising third and forth passageways, the third passageway communicating with said upper conduit and the fourth passageway communicating with said lower conduit, whereby the second passageway system simultaneously directs gas from the upper conduit to the valve chamber through said third passageway and draws liquid from the lower conduit to said valve chamber through said fourth passageway for atomization of said liquid with said gas in said valve chamber when said valve spool is aligned for nebulization; and an orifice communicating said valve chamber with said liquid holding chamber above the liquid level.

3. A combination nebulizer and humidifier unit, comprising:
- an enclosed container having outlet means and a liquid supply reservoir;
- gas inlet means;
- orifice means;
- conduit means; and
- a valve and gas nozzle component including in combination a unitary valve means and at least in part a nozzle assembly having said orifice means, said orifice means being in communication with said enclosed container above said liquid supply reservoir, said valve means upstream of said orifice means having selective positions, a gas passage defined therein, and a gas outlet port for changing the path of gas flow from said gas inlet means whereby selection of one of said positions closes said gas outlet port and causes gas from said gas inlet means to flow into said orifice means which in turn causes liquid from said liquid supply reservoir to flow through said conduit means which extends from said nozzle assembly to said reservoir into said nozzle assembly whereupon the liquid is converted to aerosol which passes out through said outlet means and whereby selection of another one of said positions causes gas from said gas inlet means to bypass said orifice means and flow through said gas outlet port and through said conduit means into the liquid in said liquid supply reservoir whereupon the gas is humidified and passed out through said outlet means.

4. A combination nebulizer and humidifier unit, comprising:
- separately formed components including a container component, a cover component, and a valve component;
- said cover component enclosing said container component and said cover component and said container component defining a liquid supply reservoir adjacent a lower portion of said cover component;
- said cover component including a receptacle having a spray orifice extending into said container component above said liquid reservoir, a gas inlet conduit in communication with said receptacle, a dual purpose conduit in communication at one end with said receptacle and in communication at said other end with said liquid supply reservoir, and outlet means above said liquid supply reservoir; and
- said valve component rotatably mounted in said receptacle and defining a valve chamber, said valve component defining first and second valve passageways adapted for selective alignment with said gas inlet conduit and said dual purpose conduit and a gas orifice coaxial with and spaced from said spray orifice whereby selective alignment of said first valve passageway causes gas from said gas inlet conduit to flow into said gas orifice and liquid from said liquid supply reservoir to rise in said dual purpose conduit into said space between said orifices thereby creating nebulization and whereby selective alignment of said second valve passageway causes gas from said gas inlet to flow through said dual purpose conduit into the liquid in said liquid supply reservoir thereby creating humidification.

5. The unit of claim 4, wherein a disseminator component is included, said disseminator positioned between said dual purpose conduit and said liquid supply reservoir and having a plurality of apertures whereby gas flowing into the liquid in said liquid supply reservoir from said dual purpose conduit passes through said apertures and into the liquid in the form of small bubbles.

6. The unit of claim 4, wherein a diffuser-baffle component is included, said diffuser-baffle component positioned within said container above said liquid supply reservoir and adjacent said spray orifice, said diffuser-baffle component including a diffuser member extending towards said spray orifice and coaxial therewith, said diffuser member and said closure component defining a path for spray emanating from said spray orifice and said diffuser-baffle component including a cylindrical baffle plate positioned in the spray path and coaxial with said diffuser.

7. The unit of claim 4, wherein said cover component includes second outlet means, a safety valve component including a disc valve covering and seated in said second outlet means, said disc valve adapted to be unseated to provide an outlet between said disc valve and second outlet means when excessive pressure exists within said container component.

8. A combination nebulizer and humidifier unit, comprising:
- an enclosed container having outlet means, a side enclosure and a liquid supply reservoir adjacent a lower portion of said side enclosure;
- said side enclosure including a receptacle having an end wall extending into said enclosed container above said liquid supply reservoir, said receptacle defining a valve housing and said end wall having a spray orifice;
- tubular means rotatably positioned within said receptacle having an end wall adjacent said other end wall, said tubular means defining a valve chamber and said end wall having a gas orifice coaxial with and spaced from said spray orifice;
- gas inlet means extending into said valve housing;
- conduit means extending from said valve housing to said liquid supply reservoir;
- a first valve inlet port and a cooperating valve outlet port selectively adapted for alignment with said gas inlet means and said conduit means respectively; and
- a second valve inlet port and a cooperating channel extending into said space between said orifices selectively adapted for alignment with said gas inlet means and said conduit means respectively whereby rotation of said tubular member to selectively align said first inlet port and said outlet port causes gas in said gas inlet means to flow into said valve chamber and on through said conduit means into the liquid in said liquid supply reservoir for humidification and whereby rotation of said tubular member to selectively align said second inlet port and said channel causes gas in said gas inlet means to flow into said vlave chamber and on through said gas orifice which in turn causes liquid from said liquid supply reservoir to rise in said conduit means and pass through said channel into said space between said orifices for nebulization.

9. The unit of claim 8, wherein the distance between said orifices is less than the diameter of said spray orifices.

10. The unit of claim 8, wherein the diameter of said gas orifice is between about 0.024 and 0.028 inch and the diameter of said spray orifice is between about 0.036 and 0.042 inch and the distance between said orifices is about 0.012 and 0.015 inch.

11. The unit of claim 8, wherein said valve ports and said channel are circumferentially spaced about said tubular means, said first valve port being spaced 90° apart from said second valve port and 180° apart from said cooperating outlet port, and said second valve port being spaced 180° apart from said channel.

12. The unit of claim 11, wherein indicator means are provided to indicate the relative position of the valve ports and channel with respect to the gas inlet means and the conduit means.

13. The unit of claim 8, wherein said enclosed container includes a diffuser-baffle assembly adjacent an upper portion of said side enclosure above said liquid supply reservoir, said diffuser-baffle assembly having a baffle to prevent oversize droplets from exiting said outlet means and a diffuser to promote aerosolization.

14. The unit of claim 13, wherein said diffuser includes a nose portion extending towards said spray orifice with the furthermost extension of said nose portion spaced from and coaxial with said spray orifice.

15. The unit of claim 14, wherein said diffuser and said end wall having said spray orifice define a path of spray for spray emanating from said spray orifice, said baffle comprising a cylindrical baffle plate open at each end and encircling said diffuser and coaxial therewith.

16. A combination nebulizer and humidifier unit, comprising:
an enclosed container having outlet means and a liquid supply reservoir;
gas inlet means;
orifice means;
conduit means; and
a valve and gas nozzle component mounted within a nozzle assembly having said orifice means, said gas nozzle being aligned with said orifice means, said orifice means being in communication with said enclosed container above said liquid supply reservoir, said valve means upstream of said orifice means having selective positions, a gas passage defined therein, and a gas outlet port for changing the path of gas flow from said gas inlet means whereby selection of one of said positions closes said gas outlet port and causes gas from said gas inlet means to flow into said gas nozzle and said orifice means which in turn causes liquid from said liquid supply reservoir to flow through said conduit means which extends from said nozzle assembly to said reservoir into said nozzle assembly whereupon the liquid is converted to aerosol which passes out through said outlet means and whereby selection of another one of said positions causes gas from said gas inlet means to bypass said orifice means and flow through said gas outlet port and through said conduit means into the liquid in said liquid supply reservoir whereupon the gas is humidified and passed out through said outlet means.

17. The unit of claim 16, wherein said valve means includes at least one outlet port, said one outlet port providing communication between said conduit means and said gas passage in said valve means whereby gas flows from said gas inlet means into said gas passage through said one outlet port into said conduit means during humidification.

18. The unit of claim 16, wherein said container includes sleeve means and said valve means is rotatably mounted in said sleeve means for movement to said selective positions.

19. The unit of claim 16, wherein a disseminator is positioned between said conduit means and said liquid supply reservoir, said disseminator having an end wall with a plurality of apertures whereupon gas flowing through said conduit means into the liquid in said liquid supply reservoir passes through said apertures and into the liquid in said liquid supply reservoir in the form of small bubbles.

20. The unit of claim 19, wherein said nozzle assembly includes a plurality of orifices and said apertures are smaller in diameter than the diameter of said orifices and the diameter of said conduit means to prevent particulate matter from said liquid supply reservoir from entering and clogging said orifices and said conduit means.

21. The unit of claim 16, wherein said enclosed container includes safety valve means above said liquid supply reservoir, said safety valve means adapted to provide an additional outlet for said enclosed container when said outlet means becomes constricted or plugged and thereby prevent an undue build-up of pressure within said enclosed container.

22. The unit of claim 21, wherein said safety valve means is adapted to provide a warning noise when gas or aerosol exits through said additional outlet.

23. The unit of claim 16, wherein said nozzle assembly includes an inner gas nozzle having an orifice and an outer spray nozzle encircling said inner gas nozzle and having an orifice spaced from and coaxial with said gas orifice.

24. The unit of claim 23, wherein the distance between said orifices is less than the diameter of said spray orifice.

25. The unit of claim 23, wherein the diameter of said gas orifice is between about 0.024 and 0.028 inch and the diameter of said spray orifice is between about 0.036 and 0.042 inch.

26. The unit of claim 25, wherein the distance between said orifices is between about 0.012 and 0.015 inch 27. The unit of claim 23, wherein a diffuser is provided within said enclosed container, said diffuser having a nose portion extending towards said orifices with the furthermost extension of said nose portion spaced from and coaxial with said spray orifice, said nose portion having a surface of revolution diverging from said furthermost extension away from said spray orifice.

28. The unit of claim 27, wherein the distance between said furthermost extension of said nose portion and said spray orifice is about 0.030 inch.

29. The unit of claim 27, wherein said diffuser and said spray nozzle define a path of spray for spray emanating from said spray orifice, a baffle plate in said enclosed container positioned in said path of spray to prevent oversize droplets of liquid from passing through said outlet means, said baffle plate comprising a cylindrical member open at each end and encircling said diffuser and coaxial with said diffuser and said spray orifice.

* * * * *